United States Patent [19]

Regnier et al.

[11] 4,264,613
[45] Apr. 28, 1981

[54] PIPERIDYLBENZIMIDAZOLINONE COMPOUNDS

[75] Inventors: Gilbert Regnier, Chatenay Malabry; Alain Dhainaut, Gennevilliers; Jacques Duhault, Croissy; Michelle Boulanger, Marly le Roi, all of France

[73] Assignee: Science Union et cie, Societe Francaise de Recherche Medicale, Suresnes, France

[21] Appl. No.: 62,878

[22] Filed: Aug. 1, 1979

[51] Int. Cl.³ .............. C07D 401/04; A61K 31/445
[52] U.S. Cl. ................................. 424/267; 546/199
[58] Field of Search ..................... 546/199; 424/267

[56] References Cited

U.S. PATENT DOCUMENTS

| | | | |
|---|---|---|---|
| 3,196,157 | 7/1965 | Janssen | 546/199 |
| 3,318,900 | 5/1967 | Janssen | 546/199 |
| 3,818,017 | 6/1974 | Janssen et al. | 546/199 |
| 3,894,030 | 7/1975 | Janssen et al. | 546/199 |
| 3,929,801 | 12/1975 | Janssen et al. | 546/199 |
| 4,080,328 | 3/1978 | Marayama et al. | 546/199 |
| 4,200,755 | 4/1980 | Grisar et al. | 546/199 |

*Primary Examiner*—Henry R. Jiles
*Assistant Examiner*—Jane T. Fan
*Attorney, Agent, or Firm*—Omri M. Behr

[57] ABSTRACT

Piperidylbenzimidazolinone compounds of the formula:

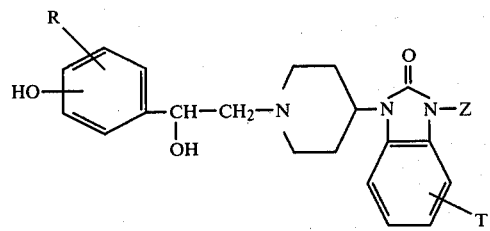

in which:
R is hydrogen, hydroxy, hydroxymethyl, methoxycarbonyl, formamido, acetamido, mesylamino, oxalamino, ethoxalylamino, carbamoyl

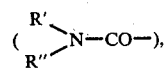

ureido

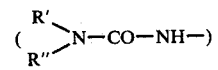

or sulfamoylamino

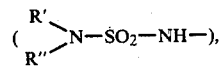

in which R' and R" are hydrogen or lower alkyl,
T is hydrogen, halogen, lower alkyl or lower alkoxy, and
Z is hydrogen, lower alkyl or lower alkenyl each in straight or branched chain.

These compounds and physiologically tolerable acid addition salts thereof may be used as medicines especially in the treatment of autoimmune, allergic and inflammatory diseases and in the treatment of respiratory insufficiency of asthma.

6 Claims, No Drawings

PIPERIDYLBENZIMIDAZOLINONE COMPOUNDS

The present invention provides piperidylbenzimidazolinone compounds of the formula:

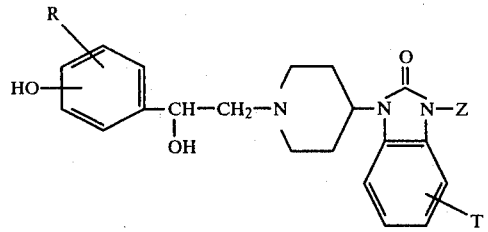

in which:

R is selected from the group consisting of a hydrogen atom, hydroxy (OH—), hydroxymethyl (HO—CH$_2$—), methoxycarbonyl (CH$_3$—O—CO—), formamido (H—CO—NH—), acetamido (CH$_3$—CO—NH—), mesylamino (CH$_3$—SO$_2$—NH—), oxalamino (HOOC—CO—NH—), ethoxalylamino (C$_2$H$_5$OOC—CO—NH—), carbamoyl

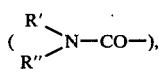

ureido

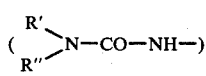

and sulfamoylamino

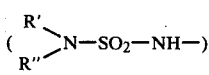

radicals, R' and R", being identical or different, are each selected from the group consisting of a hydrogen atom and alkyl radicals having from 1 to 5 carbon atoms inclusive, T is selected from the group consisting of a hydrogen atom, halogen atoms and alkyl and alkoxy radicals each having from 1 to 5 carbon atoms inclusive, and Z is selected from the group consisting of a hydrogen-atom and alkyl and alkenyl radicals each having from 1 to 5 carbon atoms inclusive in straight and branched chain.

In the here above-definitions, there may be mentioned for example as halogen atoms: chlorine, bromine and fluorine atoms, as alkyl radicals: methyl, ethyl, propyl, butyl and pentyl radicals, as alkoxy radicals: methoxy, ethoxy, propoxy, butoxy and pentyloxy radicals, and as alkenyl radicals: allyl, isopropenyl, butenyl and pentenyl radicals.

The present invention also provides acid addition salts of the compounds of the general formula I. The acid addition salts are preferably physiologically tolerable acid addition salts.

The present invention further provides a process for preparing the compounds of the general formula I which comprises reacting a haloacetophenone of the general formula II:

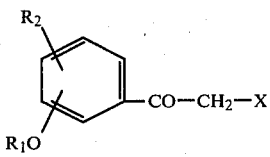

in which:

X is selected from the group consisting of a chlorine and a bromine atom,

R$_1$ is selected from the group consisting of a hydrogen atom, and easily hydrolysable or hydrogenisable protecting groups, such for example as acetyl and benzyl radicals, and R$_2$ is selected from the group consisting of a hydrogen atom and hydroxy, acetoxy, benzyloxy, hydroxymethyl, acetoxymethyl, benzyloxymethyl, methoxycarbonyl (CH$_3$—O—CO—), formamido (H—CO—NH—), acetamido (CH$_3$—CO—NH—), mesylamino (CH$_3$—SO$_2$—NH—), oxalamino (HOOC—CO—NH—), ethoxalylamino (C$_2$H$_5$OOC—CO—NH—), carbamoyl

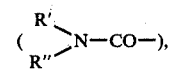

ureido

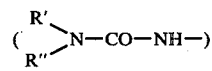

and sulfamoylamino

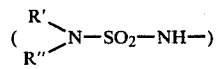

radicals, R' and R" being as previously defined, with a piperidylbenzimidazolinone of the general formula III:

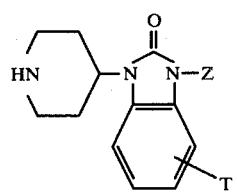

in which Z and T have the meanings given above, then reducing the so-obtained compound of the general formula IV:

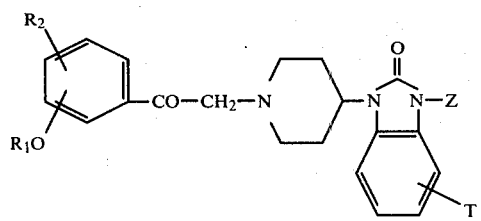

in which R$_1$, R$_2$, T and Z have the meanings given above, and when the reduced compound contains some protecting groups, eliminating these protecting groups according to known methods.

Such a process is advantageously carried out by reacting the compounds II and III in solution in a polar solvent such for example as an aliphatic alcohol or ketone having 4 or 5 carbon atoms, or dimethylformamide, at a temperature within the range of from 110° to 140° C., in the presence of an acceptor of the hydrohalide formed during the reaction. As acceptors, there may be mentioned, for example, alkali metal salts of carbonic acid, such for example as, sodium or potassium carbonate, or an excess of the piperidylbenzimidazolinone of the formula III, the excess acting as the acid acceptor.

The reduction of the compound IV is advantageously performed with an alkali metal hydride such for example as sodium borohydride ($BH_4Na$), potassium borohydride ($BH_4K$) or sodium cyanoborohydride ($BH_3CN\,Na$), in a polar solvent such for example as a water mixible aliphatic alcohol or tetrahydrofuran. It is also advantageous to carry out this reduction with hydrogen at a pressure within the range of 5 to 70 atmospheres in the presence of a catalyst containing a group VIII metal such as palladium on charcoal, platinum or nickel, in a polar solvent such for example as a water mixible aliphatic alcohol, at a temperature within the range of from 25° to 80° C.

The protecting group/or groups which may exist in the so-obtained reduced compound IV, may be then eliminated, according to known methods, either by a mild acid hydrolysis (especially for acetyl group), or by a hydrogenolysis in the presence of a catalyst such for example as palladium on charcoal or platinum, under a hydrogen atmosphere (for benzyl group).

The haloacetophenones of the general formula II are either known and described in literature, or prepared according to the method described by LARSEN and al, J. Med. Chem. 10,462 (1967).

1-(4-piperidyl)benzimidazolin-2-ones of the general formula III are prepared starting from the corresponding 1-(1-triphenylmethyl-4-piperidyl)benzimidazolin-2-ones.

1-(4-piperidyl)benzimidazolin-2-one is a trade product.

The present invention also provides a process for preparing compounds of the general formula I which comprises an alkylating reduction of a mixture of a piperidylbenzimidazolinone of the formula III as defined above, and a phenylglyoxal of the general formula V:

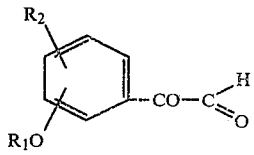
V in which $R_1$ and $R_2$ have the meanings given above.

Such an alkylating reduction is advantageously carried out, according to a method analogous to the one described by G. FODOR and al, Am. Soc. 71,1045 (1949), by operating under a hydrogen pressure within the range of from 5 to 10 atmospheres in the presence of a catalyst selected from VIII group metals such for example as platinum or palladium on charcoal, in a polar solvent such as a water mixible aliphatic alcohol, at a temperature within the range of from 25° to 80° C.

The protecting group/or groups which may exist in the compound V are cleft during the reduction. Nevertheless, for acetyl compounds, it is suitable to perform the reduction in diluted acid medium.

Phenylglyoxals of the general formula V are either known and described in literature, or prepared according to the method described by G. FODOR and al, Am. Soc. 71, 1045 (1949).

The present invention also provides a process for preparing compounds of the general formula I which comprises reacting a piperidylbenzimidazolinone of the formula III as defined above, with a halohydrin of the general formula VI

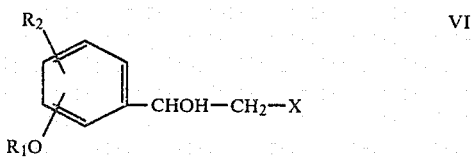
VI in which X, $R_1$ and $R_2$ have the meanings given above.

Such a reaction is advantageously carried out in a polar solvent such for example as an aliphatic alcohol having 4 or 5 carbon atoms or dimethylformamide at a temperature within the range of from 110° to 140° C., in the presence of an acceptor of the hydrohalide formed during the reaction. As acceptors, there may be mentioned for example alkali metal salts of carbonic acids, such for example as sodium or potassium carbonate, or an excess of the piperidylbenzimidazolinone of the formula III, the excess acting as the acid acceptor.

The protecting group/or groups which may exist in the product of condensation may be then eliminated according to the known methods given above.

The starting halohydrins of the general formula VI are prepared for example starting from the corresponding haloacetophenones of the general formula II by reducing them with an alkali metal borohydride. They are generally used in the raw state, without purification.

The compounds of the general formula I obtained according to the above processes are amphoteric weak base soluble in strong acids and bases.

The present invention provides addition salts of the compounds of the general formula I, especially addition salts with strong acids, and more particularly physiologically tolerable acid addition salts. As acids which may be used for the formation of these salts there may be mentioned for example hydrochloric, hydrobromic, sulfuric, methanesulfonic and isethionic acids.

The compounds of the formula I and physiologically tolerable salts thereof possess valuable, pharmacological and therapeutic properties, especially bronchodilating, β-adrenergic and anti-allergic properties.

Their toxicity is low and their $LD_{50}$ determined in mice is higher than 1600 mg/kg per oral route or higher than 200 mg/kg by intraperitoneal route, according to the compounds.

The bronchodilating activity was studied in the guineapig by the method of H. KONZETT and R. ROSSLER Arch. Exp. Path. U.Pharm. 195, 71 (1940). The compound of example 1, which is 1-[2-(3,4-dihydroxyphenyl)-2-hydroxy]ethyl-4-(2-oxo benzimidazolin-1-yl)piperidine, injected intravenously at a dose within the range of from 0.010 to 0.050 mg/kg inhibits totally the bronchospasm cause by an intravenous administration of either histamine, serotonin or acetylcholine, and the effect of Slow Reacting Substance, at a dose within the range of from 0.050 to 0.100 mg/kg. For the other compounds of the invention such a complete inhibition of the bronchospasm is observed at doses which may vary from 0.5 to 10 mg/kg by intravenous route according to the compounds.

Submitted to the test of A. K. ARMITAGE, Brit. J. Pharmacol. 17, 196 (1961), the compounds of the present invention, administered by intra-peritoneal route at doses which vary from 0.5 to 20 mg/kg according to the compounds, inhibit 50% of the effect produced in the guinea-pig by an aerosol of histamine at 4%.

The compounds of the present invention administered by intra-peritoneal route at doses within the range of from 5 to 20 mg/kg inhibit 50% of the anaphylactic shock provoked by the administration of an aerosol at 5% of albumin to guinea-pigs previously made sensitive to albumin. This test, performed for each compound to be tested on a batch of 6 guinea-pigs, was carried out as follows:

The guinea-pigs were submitted to an intra-peritoneal injection of 100 mg/kg of ovalbumin emusified in the Freund adjuvant. Four weeks later, a selection of sensitized guinea-pigs is performed as follows: the animals, fasted since the day before, are treated with an aerosol containing 5% of ovalbumin, and the times before the appearance of a deep dyspnea then pre-coma are noted. There were then selected, for the following tests, the guinea-pigs for which a deep dyspnea appears less than 3 minutes after the beginning of the treatment with the aerosol of ovalbumin. Eight days later, the compounds to be tested are injected by intraperitoneal route to these selected guinea-pigs fasted since the day before, then twenty minutes later these guinea-pigs are submitted to an aerosol containing 5% of ovalbumin. The times before the appearance of a deep dyspnea then pre-coma are noted and the protecting action of the tested compounds is so determined.

Furthermore, an action on the passive cutaneous anaphylaxis provoked in the rats according to Ovary's technique (Prog. Allergy 5, 459-508, S. Karger Basel/-New-York), was observed when the compounds of the invention are administered by intravenous route at doses within the range of from 0.050 to 2.5 mg/kg according to the compounds.

The above pharmacological properties and the low toxicity of compounds of the general formula I and physiologically tolerable salts thereof enable their use in therapy especially in the treatment of all the diseases in which it is necessary to inhibit the antigen-antibody reactions such as autoimmune, allergic and antiinflammatory diseases and more particularly diseases in which an additional β-adrenergic effect is wellcome such as asthmatic dyspnea.

The present invention also provides pharmaceutical compositions comprising as active ingredient a compound of the formula I or a physiologically tolerable addition salts thereof, in admixture or conjunction with a pharmaceutically suitable carrier, and more particularly with a carrier suitable for an administration by aerosol:

The so-obtained pharmaceutical compositions are advantageously in unit dosage forms such for example as tablets, dragees, capsules, suppositories, injectable or drinkable solutions, or aerosols. For a guidance, the compound of example I may be used at doses within the range of from 100 to 750γ of active ingredient by puff.

The following examples illustrate the invention, the melting points being determined in a capillary tube unless otherwise stated.

EXAMPLE 1

1-[2-(3,4-dihydroxyphenyl)-2-hydroxy]ethyl-4-(2-oxobenzimidazolin-1-yl)piperidine

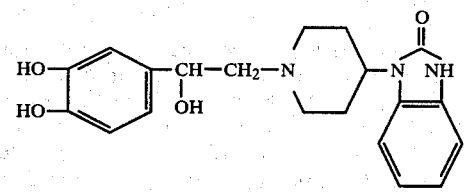

First method

A suspension of 6.87 g of 3,4-dihydroxyphenyl chloromethylketone (trade product) and 8 g of 4-(2-oxobenzimidazolin-1-yl)piperidine (trade product), M.P. 183°–185° C., in 640 ml of methylethyl ketone, in the presence of 1.95 g of dried sodium carbonate and 0.1 g of sodium iodide, was refluxed for 12 hours. After the completion of the reaction, the precipitate was filtered off and washed with water. After drying, there were obtained 14 g of raw base which is transformed in hydrochloride in methanol by addition of hydrochloric ether. There were obtained 8 g of 1-(3,4-dihydroxy phenacyl)-4-(2-oxobenzimidazolin-1-yl)piperidine hydrochloride, white crystals melting at 310°–313° C.

A solution of 7 g of the so-obtained hydrochloride in 770 ml of ethanol at 90%, was hydrogenized for 6 hours in the presence of 10 g of palladised charcoal containing 10% in weight of palladium, under a hydrogen pressure of 70 atmospheres.

After the completion of the reduction, the catalyst was filtered off, the solvent was evaporated under reduced pressure and the so-obtained hydrochloride was taken up with an aqueous solution containing 10% of Na H CO₃. There were finally obtained 2.5 g of 1-[2-(3,4-dihydroxyphenyl)-2-hydroxy]ethyl-4-(2-oxobenzimidazolin-1-yl)piperidine, beige crystals melting at 216°–217° C.

Second method

A solution of 11.5 g of 3,4-dibenzyloxyphenol glyoxal, M.P. 98° C. (prepared according to the technique described by G. Fodor and al. Am. Soc. 71, 1045, (1949) and 7.25 g of 4-(2-oxobenzimidazolin-1-yl)piperidine in 500 ml of ethanol at 90% was hydrogenized under 5 atmospheres in the presence of 5 g of palladised charcoal containing 10% in weight of palladium. When the theoretical amount of hydrogen was absorbed, the catalyst was filtered off and the solvent evaporated under reduced pressure. The crystalline residue was stirred with twice 50 ml of boiling water, then filtered off and dissolved in 100 ml of a normal solution of monomethanesulfonic acid.

The insoluble matter was extracted with chloroform and the aqueous acid solution was alkalized until pH 8 with sodium bicarbonate. The base precipitated out. After washing with water and drying, there were obtained 6 g of 1-[2-(3,4-dihydroxyphenyl)-2-hydroxy]ethyl-4-(2-oxobenzimidazolin-1-yl)piperidine, beige crystals melting at 215°–216° C.

Third method

A solution of 8.4 g of 1-(3,4-dihydroxyphenyl)-2-chloro-1-ethanol, M.P. 102° C., (prepared starting from 3,4-dihydroxyphenyl chloromethyl ketone according to a method similar to O. Hinsberg's technique. German Pat. No. 364.039 of Nov. 16, 1922) and 10.8 g of 4-(2-oxobenzimidazolin-1-yl)piperidine in 250 ml of butanol was refluxed for 8 hours in the presence of 6.9 g of potassium carbonate.

After the completion of the reaction, the so-formed salt was filtered off and the solvent evaporated under reduced pressure. The residue was then stirred with twice 50 ml of boiling water, then filtered off and dissolved in 100 ml of a normal solution of monomethane-sulfonic acid. The insoluble matter was extracted with chloroform and the aqueous acid solution was alkalized until pH 8 with sodium bicarbonate. The base precipitated out. After washing with water and drying, there were obtained 9 g of 1-[2-(3,4-dihydroxyphenyl)-2-hydroxy]ethyl-4-(2-oxobenzimidazolin-1-yl)piperidine, beige crystals melting at 215°–216° C.

EXAMPLE 2 TO 14

The following compounds were prepared according to the methods described in example 1:

(2) 1-[2-(4-hydroxyphenyl)-2-hydroxy]ethyl-4-(2-oxobenzimidazolin-1-yl)piperidine, M.P. 213°–215° C., (methyl cyanide).

(3) 1-[2-(3,5-dihydroxyphenyl)-2-hydroxy]ethyl-4-(2-oxobenzimidazolin-1-yl)piperidine, M.P. of its hydroxhloride: 256°–260° C. (ethanol).

(4) 1-[2-(3-hydroxymethyl-4-hydroxyphenyl)-2-hydroxy]ethyl-4-(2-oxobenzimidazolin-1-yl)piperidine, M.P. of its hydrochloride 360° C. (ethanol). (5) 1-[2-(3-methoxycarbonyl-4-hydroxy phenyl)-2-hydroxy]ethyl-4-(2-oxobenzimidazolin-1-yl)piperidine, M.P. 206°–209° C. (methanol).

(6) 1-[2-(3-carbamoyl-4-hydroxyphenyl)-2-hydroxy]ethyl-4-(2-oxobenzimidazolin-1-yl)piperidine.

(7) 1-[2-(3-ureido-4-hydroxyphenyl)-2-hydroxy]ethyl-4-(2-oxobenzimidazolin-1-yl)piperidine, M.P. 214°–218° C. (ethanol).

(8) 1-[2-(3-sulfamoylamino-4-hydroxy phenyl)-2-hydroxy]ethyl-4-(2-oxobenzimidazolin-1-yl)piperidine, M.P. of its hydrochloride: 188° C. ethanol/water—90/10).

(9) 1-[2-(3-mesylamino-4-hydroxy phenyl)-2-hydroxy]ethyl-4-(2-oxobenzimidazolin-1-yl)piperidine, M.P. of its hydrochloride: 230°–233° C. (ethanol).

(10) 1-[2-(3-ethoxalylamino-4-hydroxyphenyl)-2-hydroxy]ethyl-4-(2-oxobenzimidazolin-1-yl)piperidine.

(11) 1-[2-(3-oxalamino-4-hydroxyphenyl)-2-hydroxy]ethyl-4-(2-oxobenzimidazolin-1-yl)piperidine, M.P. 258°–260° C. (water).

(12) 1-[2-(3-formamido-4-hydroxyphenyl)-2-hydroxy]ethyl-4-(2-oxobenzimidazolin-1-yl)piperidine, M.P. of its hydrochloride hemihydrate: 266°–270° C. (water).

(13) 1-[2-(3,4-dihydroxyphenyl)-2-hydroxy]ethyl-4-(3-methyl-2-oxobenzimidazolin-1-yl)piperidine, M.P. 244°–246° C., M.P. of its hydrochloride monohydrate: 178°–186° C. (ethanol at 95%).

The starting 4-(3-methyl-2-oxobenzimidazolin-1-yl)piperidine, M.P. of its carbonate: 145°–150° C., was prepared starting from 1-triphenylmethyl-4-(3-methyl-2-oxobenzimidazolin-1-yl)piperidine, M.P. 284°–289° C., itself prepared starting from 1-triphenylmethyl-4-(2-oxobenzimidazolin-1-yl)piperidine, M.P. 292°–296° C.

(14) 1-[2-(3,4-dihydroxyphenyl)-2-hydroxy]ethyl-4-(3-allyl-2-oxobenzimidazolin-1-yl)piperidine.

We claim:
1. A compound selected from the group consisting of: piperidylbenzimidazolinone compounds of the formula:

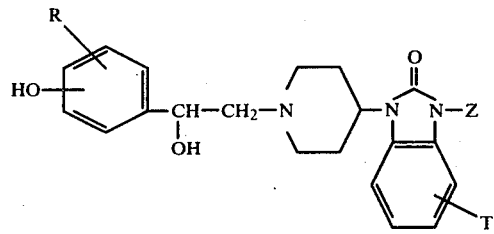

in which:
R is selected from the group consisting of hydrogen, hydroxy (OH—), hydroxymethyl (HO—CH$_2$—), formamido (H—CO—NH—), acetamido (CH$_3$—CO—NH—), mesylamino (CH$_3$—SO$_2$—NH—), oxalamino (HOOC—CO—NH—), ethoxalylamino (C$_2$H$_5$OOC—CO—NH—), ureido

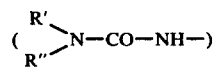

and sulfamoylamino

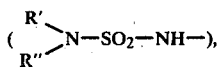

R' and R", being identical or different, are each selected from the group consisting of hydrogen and alkyl having from 1 to 5 carbon atoms inclusive, T is selected from the group consisting of hydrogen, halogen, alkyl and alkoxy each having from 1 to 5 carbon atoms inclusive, and Z is selected from the group consisting of hydrogen, alkyl and alkenyl each having from 1 to 5 carbon atoms inclusive in straight and branched chain; and physiologically tolerable salts thereof.

2. A compound of claim 1 which is 1-[2-(3,4-dihydroxyphenyl)-2-hydroxy]ethyl-4-(2-oxobenzimidazolin-1-yl)piperidine.

3. A compound of claim 1 which is 1-[2-(4-hydroxyphenyl)-2-hydroxy]ethyl-4-(2-oxobenzimidazolin-1-yl)piperidine.

4. A compound of claim 1 which is 1-[2-(3,5-dihydroxyphenyl)-2-hydroxy]ethyl-4-(2-oxobenzimidazolin-1-yl)piperidine and its hydrochloride.

5. A pharmaceutical composition having broncodilating, β-adrenergic and anti-allergic activity containing an effective amount of a compound of claim 1 as active ingredient, together with a suitable physiologically acceptable carrier.

6. A method for treating a living animal body afflicted with antoimmune allergic or anti-inflammatory diseases or asthmatic dyspnea, comprising the step of administering an amount of a compound of claim 1 which is effective for the alleviation of the said condition.

* * * * *

Notice of Adverse Decision in Interference

In Interference No. 101,009, involving Patent No. 4,264,613, G. Regnier, A. Dhainaut, J. Duhault and M. Boulanger, PIPERIDYLBENZIMIDAZOLINONE COMPOUNDS, final judgment adverse to the patentees, was rendered June 14, 1983, as to claims 1 and 2.

[*Official Gazette* November 15, 1983.]